United States Patent [19]

Rohrbach et al.

[11] 4,382,121

[45] May 3, 1983

[54] PRETREATMENT OF GLUCOSE FEEDSTOCK

[75] Inventors: Ronald P. Rohrbach, Lake Forest; Mary J. Maliarik, Lake Forest, both of Ill.

[73] Assignee: UOP Inc., Des Plaines, Ill.

[21] Appl. No.: 261,995

[22] Filed: May 8, 1981

[51] Int. Cl.$^3$ .......................... C12P 7/00; C12P 19/24
[52] U.S. Cl. ...................................... 435/94; 435/174; 426/48; 127/46.1; 127/30
[58] Field of Search ................. 435/94, 184, 234, 161, 435/162, 188, 105, 174; 426/48; 127/52, 46.1, 50, 51, 30, 37

[56] References Cited

U.S. PATENT DOCUMENTS

| Re. 28,885 | 6/1976 | Cotter et al. | 435/94 |
| 1,580,136 | 4/1926 | Hamburger et al. | 127/46.1 X |
| 4,242,145 | 12/1980 | Muller et al. | 127/46.1 X |
| 4,310,628 | 1/1982 | Leiser | 435/94 |

OTHER PUBLICATIONS

Wen-Pin Chen, Glucose Isomerase (a Review), Process Biochemistry, Aug./Sep. 1980, p. 36.
Chem. Abstracts 60:14860c-h, 1964.

*Primary Examiner*—Kenneth M. Schor
*Attorney, Agent, or Firm*—James R. Hoatson, Jr.; Eugene I. Snyder; William H. Page, II

[57] ABSTRACT

Commercial glucose solutions used as feedstock for enzymatic conversion of glucose to fructose by glucose isomerase often contain materials which act as poisons toward the enzyme. It has been found that these poisons can be removed, or destroyed, by treatment of the feedstock with oxidizing agents, chief of which is hydrogen peroxide.

9 Claims, No Drawings

PRETREATMENT OF GLUCOSE FEEDSTOCK

BACKGROUND OF THE INVENTION

Fructose, or grape sugar, has been used as a sugar substitute in many applications. Increasing sugar prices spur increased fructose usage, and current fructose production is at an all-time peak.

The largest commercial source of fructose is glucose, an end product of starch hydrolysis, which is isomerized to fructose by enzymatic methods using glucose isomerase. Because the high enzyme cost dictates it reusability, the isomerization is not done homogeneously, where recovery of enzyme would be difficult and costly, but instead is performed heterogeneously using glucose isomerase immobilized in some manner. That is, either cells containing glucose isomerase, or the enzyme itself, is physically and/or chemically bound to a support through which flows a glucose feedstock, with isomerization of glucose to fructose attending contact of the feedstock with the immobilized glucose isomerase system (IMGI).

It is highly desirable to have the IMGI as productive as possible. A measure of its productivity is its half-life, by which is meant the time necessary to reduce the activity of an IMGI to one-half its initial value. We have repeatedly observed that the half-life of an IMGI was substantially longer using a purified glucose feedstock than with a commercial feedstock. These observations led to the discovery that the deleterious effect on IMGI half-life was directly associated with the presence of carbonyl-containing components in the feedstock which formed a precipitate with 2,4-dinitrophenylhydrazine. It was further discovered that removal of these components, or poisons, from the feedstock led to a substantial increase in the half-life, and thus the productivity, of IMGI. A crucial discovery leading to the invention described herein is that certain oxidizing agents very effectively chemically alter these poisons, or deleterious components, in a glucose feedstock, thereby rendering them innocuous and, in effect, removing the poisons initially present.

SUMMARY OF THE INVENTION

An object of this invention is to increase the productivity of immobilized glucose isomerase systems. An embodiment comprises treating a glucose feedstock with an oxidizing agent at a pH from about 6 to about 9. In a more specific embodiment the oxidizing agent is hydrogen peroxide. In a still more specific embodiment the oxidizing agent is hydrogen peroxide used at a pH from about 7.5 to about 9.

DESCRIPTION OF THE INVENTION

The invention claimed herein is a process of treating a glucose feedstock prior to enzymatic conversion to fructose comprising contacting the feedstock with an effective amount of an oxidizing agent at a pH from about 6 to about 9 at a temperature from about 0° to about 80° C. It has been found that such treatment substantially increases the productivity of the enzyme glucose isomerase when used in an immobilized enzyme system, such increasing productivity being manifested by an increased half-life of the IMGI.

The problem which this invention solves is that commercial glucose feedstocks for fructose formation via IMGI frequently contain poisons which substantially reduce the productivity of IMGI as manifested by its half-life. For example, if an IMGI has a half-life of 70 to 80 days with a purified glucose feedstock, the IMGI may have a half-life of only from about 25 to 40 days with a commercial glucose feedstock. For the purpose of this application, the term "poisons" refers to materials found in commercial glucose feedstocks which contribute to a decrease in half-life of immobilized glucose isomerase.

A characteristic common to all glucose feedstocks exhibiting a deleterious effect on the half-life is the presence of components in minor amounts which form precipitates with 2,4-dinitrophenylhydrazine. Although the nature of these minor components is not known with certainty, it was possible to qualitatively correlate their amount, via their derivatives with 2,4-dinitrophenylhydrazine, with the extent of the reduction in half-life of IMGI. Thus, the greater the amount in the feedstock of components which form derivatives with 2,4-dinitrophenylhydrazine, the less was the half-life of the IMGI. It also was observed that when the feedstock in which such components were initially absent was treated so as to induce formation of these components, the resulting feedstock substantially reduced the half-life of IMGI.

An inference which may be drawn from these observations is that the minor components forming precipitates with 2,4-dinitrophenylhydrazine are themselves poisons, or that the presence of the poisons is associated with the presence of the minor components. Although it is unknown which inference is the more correct one, this invention may be successfully practiced nonetheless. Similarly, although at least one of the minor components may be a 3-deoxyhexosone it is not known unequivocally that this is present when precipitates form with 2,4-dinitrophenylhydrazine, nor is its effect as a poison independently known.

It was subsequently discovered that treating the feedstock containing the poisons with certain oxidizing agents destroy the aforementioned minor components, with the treated feedstock showing no deleterious effect on enzyme productivity. This discovery led to the process of this invention, which is essentially a method of removing certain minor components from a glucose feedstock, components whose presence have a deleterious effect on the productivity of the IMGI.

The process of this invention comprises contacting a feedstock with an effective amount of oxidizing agent. Among the oxidizing agents which may be used in the process of this invention are hydrogen peroxide, other peroxides, hypohalites, especially hypochlorites and hypobromites, perhalates, especially perchlorates and perbromates, and persulfates. Hydrogen peroxide is a highly preferred oxidizing agent. Other preferred oxidizing agents include the alkali metal and alkaline earth salts of hypochlorites and perchlorates.

The amount of oxidizing agent effective in the practice of this invention depends somewhat on the oxidizing agent, the amount of poison present in the feed, and the pH at which treatment is performed. Generally, the oxidizing agent of this invention will be effective in amounts from about 50 to about 500 ppm. In particular, when hydrogen peroxide is used at a pH from about 7.5 to about 9, an amount from about 50 to about 250 ppm constitutes an effective amount, and an amount from about 100 to about 200 ppm is even more desirable. As the pH decreases, the amount necessary to be effective in the practice of this invention increases.

As previously stated, the process of this invention is pH dependent. It is found that the lower the pH, the greater must be the amount of oxidizing agent used. On the other hand, it is found that at a pH greater than about 9 there are formed color bodies which are undesirable from a commercial aspect. Thus, a pH range from about 6 to about 9 is desirable in the practice of this invention, and the range from about 7.5 to about 9 is preferred.

The contact time is dependent upon the temperature, pH, the amount of oxidizing agent used, and the amount of undesirable component present. A temperature from about 10° to about 80° C. may be employed, but a range from about 50° to about 70° C. is preferred to minimize contact time without adversely effecting the feedstock. At a pH of about 9 with about 200 ppm hydrogen peroxide, a contact time of about 90 minutes at 20° C., or 20 minutes at 60° C., is adequate to maximize the beneficial effects of the process of this invention. It is to be understood that at a different pH and/or using a different oxidizing agent, the necessary contact time may differ from that stated above, but can be readily determined through simple experimentation.

Where it is necessary to remove residual oxidizing agent prior to contacting the glucose feedstock with IMGI, this may be done by treating the feedstock with bisulfite, sulfite, charcoal, iron (ferrous or ferric), or catalase. For example, feedstock with residual oxidizing agent may be passed through a bed of charcoal. As another example, residual oxidizing agent may be removed by adding a sulfite to the glucose feedstock. When this latter mode of treatment is chosen, it is found that from about 100 to about 1000 ppm of sulfite is preferred to be added.

The examples below are merely illustrative of this invention which is not to be limited thereto.

EXAMPLE I

In all the examples IMGI was a preparation where glucose isomerase was immobilized onto a support matrix comprised of alumina impregnated with polyethylenimine subsequently cross-linked with excess glutaraldehyde so as to furnish excess pendant aldehyde groups. Reactors were of the fixed bed type operated at 60° C. with feedstock in an upflow mode and a space velocity sufficient to afford 42% fructose in the effluent.

In this example two reactors were run in series. The feedstock was 45% weight/weight purified glucose (Cerelose TM) containing 0.1% sodium sulfite and 7 ppm sodium omadine at pH 8.0. The feedstock gave no precipitate when treated with 2,4-dinitrophenylhydrazine. It had been found by independent experimentation that passage of the purified feedstock through IMGI caused formation of undesirable minor components. In this example the normal mode of operation consisted of passing the feedstock through the first reactor, then using the effluent from the first reactor as the feedstock for the second reactor. In this mode the second reactor performed only a small chemical change to 48% fructose, since the feedstock at 42% fructose already was near equilibrium for the liquid hourly space velocity used. However, the second reactor was exposed to poisons formed in the first reactor. Periodically, the second reactor was fed with the purified glucose feedstock and its activity measured. This was done solely in order to determine its half-life. It was found that the half-life of the first reactor was about 144 days, whereas the half-life of the second reactor was about 84 days.

This experiment isolates and demonstrates the effect of poisons in the feedstock on the half-life of IMGI.

EXAMPLE II

Commercial feedstock containing operationally appreciable amounts of poisons, as determined by formation of 2,4-dinitrophenylhydrazine derivatives, was treated with varying amounts of hydrogen peroxide at pH 9 for 90 minutes at room temperature. When the peroxide was used at a concentration greater than about 100 ppm no observable precipitate formed. When the peroxide was used at levels between 25 and 50 ppm an observable precipitate formed. When peroxide was absent a fairly heavy precipitate formed. Thus, poisons were present at a level requiring at least 50 to about 100 ppm of oxidizing agent in this particular feedstock.

EXAMPLE III

A portion of a commercial feedstock was treated for 90 minutes at ambient temperature and pH 9.0 with 200 ppm hydrogen peroxide. Excess peroxide was destroyed by addition of 1000 ppm sodium sulfite and the pH was adjusted to 8.2. Another portion of the feedstock was treated identically except hydrogen peroxide was omitted. The two feedstocks were used in two reactors operating in tandem to determine half-life of the IMGI. Results are given below.

|  | Hydrogen Peroxide Treated Feed | Untreated Feed |
| --- | --- | --- |
| Initial Activity (units per gram) | 1500 | 1370 |
| Half-Life (days) | 74 | 38 |

Thus, hydrogen peroxide treatment increases the half-life of IMGI by a factor of almost two relative to untreated material.

What is claimed is:

1. In a method of converting glucose to fructose using an immobilized glucose isomerase system, the improvement wherein a feedstock containing glucose and minor amounts of isomerase poisons, prior to contacting with the immobilized glucose isomerase system, is treated with an oxidizing agent selected from the group consisting of peroxides, hypohalites, perhalates, and persulfates at a pH from about 6 to about 9 at a temperature from about 10° to about 80° C. for a time and in an amount effective to increase the productivity of said immobilized glucose isomerase system above that productivity occurring when the enzymatic isomerization is carried out without the presence of said oxidizing agent, the treatment being for a time sufficient to destroy said poisons.

2. The process of claim 1 where the oxidizing agent is hydrogen peroxide.

3. The process of claim 1 where the oxidizing agent is a hypochlorite.

4. The process of claim 1 where the oxidizing agent is a perchlorate.

5. The process of claim 1 where the pH is between about 7.5 and about 9.

6. The process of claim 1 where the temperature is from about 50° to about 70° C.

7. The process of claim 1 further characterized in that residual oxidizing agent is removed prior to said enzymatic conversion.

8. The process of claim 1 where the effective amount is from about 50 to about 500 ppm.

9. The process of claim 1 where the amount is from about 50 to about 250 ppm.